United States Patent [19]

Bonnell

[11] Patent Number: 4,863,133

[45] Date of Patent: Sep. 5, 1989

[54] ARM DEVICE FOR ADJUSTABLE POSITIONING OF A MEDICAL INSTRUMENT OR THE LIKE

[75] Inventor: Leonard Bonnell, Huntingdon Valley, Pa.

[73] Assignee: Leonard Medical, Huntingdon Valley, Pa.

[21] Appl. No.: 54,431

[22] Filed: May 26, 1987

[51] Int. Cl.$^4$ .............................................. F16M 11/14
[52] U.S. Cl. ...................................... 248/278; 267/83; 403/56; 248/280.1; 248/288.3; 248/563
[58] Field of Search .................... 248/278, 284, 280.1, 248/288.3, 292.1, 291, 81, 138, 481, 123.1, 654, 563, 567; 267/83; 403/55, 56, 32, 5

[56] References Cited

U.S. PATENT DOCUMENTS

| | | |
|---|---|---|
| 205,069 | 6/1878 | Farnsworth . |
| 652,789 | 7/1900 | Leitelt, Jr. . |
| 1,460,697 | 3/1922 | Bendlin . |
| 2,827,312 | 3/1958 | Spencer ................................. 285/18 |
| 3,003,389 | 8/1960 | Desbrow ............................... 188/73 |
| 3,221,845 | 12/1965 | Hansen .................................. 188/171 |
| 3,491,230 | 1/1970 | Lory ....................................... 240/1.4 |
| 3,638,973 | 2/1972 | Poletti .................................... 285/184 |
| 3,795,290 | 3/1974 | Hori et al. ............................. 188/76 |
| 3,858,578 | 1/1975 | Milo ....................................... 128/20 |
| 3,874,706 | 4/1975 | Arnold ................................... 285/24 |
| 3,971,538 | 7/1976 | Marvich ................................ 248/278 |
| 3,986,692 | 10/1976 | Kinoshita .............................. 248/160 |
| 4,045,054 | 8/1977 | Arnold . |
| 4,158,462 | 6/1979 | Coral ..................................... 285/168 |
| 4,165,530 | 8/1979 | Sowden ........................ 248/280.1 X |
| 4,166,602 | 9/1979 | Nilsen et al. ........................ 248/280.1 |
| 4,181,201 | 1/1980 | McCarthy ............................. 188/171 |
| 4,185,801 | 1/1980 | Plymoth ................................. 248/289 |
| 4,328,799 | 5/1982 | LoPiano . |
| 4,344,595 | 8/1982 | Heller et al. .......................... 248/542 |
| 4,364,535 | 12/1982 | Itoh et al. ............................. 248/123.1 |
| 4,397,439 | 8/1983 | Wilbur et al. ....................... 248/292.1 |
| 4,402,481 | 9/1983 | Sasaki .................................... 403/55 X |
| 4,457,300 | 7/1984 | Budde .................................... 128/20 |
| 4,466,307 | 8/1984 | Kouno ........................... 248/280.1 X |
| 4,491,435 | 1/1985 | Meier ..................................... 403/55 |
| 4,533,274 | 8/1985 | Moore .................................... 403/31 |
| 4,557,623 | 12/1985 | Tella ...................................... 403/56 X |
| 4,564,179 | 1/1986 | Hollingsworth ................. 269/83 X |
| 4,645,156 | 2/1987 | Karapita ............................ 248/280.1 |

FOREIGN PATENT DOCUMENTS 141879  4/1920  United Kingdom .

OTHER PUBLICATIONS

The Neg'ator Literature.
Sharplan 733 Literature, Advanced Surgical Technologies Inc., 1305 Wiley Rd., Suite 129, Schaumburg, IL 60195.
Biolas Literature, Advanced Biomedical Instruments, 4 Plympton St., Woburn, MA 01801.
The Zeiss Literature.

Primary Examiner—Ramon S. Britts
Assistant Examiner—Karen J. Chotkowski

[57] ABSTRACT

An instrument-supporting, articulated device has a distal end capable of supporting an instrument in the region of a surgical operating site. The device has at least one joint that supports a movable distal support element relative to a proximal support, the joint being associated with a mode selector. The joint has structure capable, upon selection of a first mode of operation by the selector, of enabling relatively free motion of the joint for achieving a desired position of the instrument and the joint has structure capable, upon selection of a second mode of operation by the selector, to set the position of the instrument in space with lightly loaded restraint. The lightly loaded restraint is of a value that, while the second mode continues to be selected, the user may adjust the position of the instrument by application of a light force to the instrument and upon release of such light force by the user, the instrument will remain in the newly adjusted position.

16 Claims, 16 Drawing Sheets

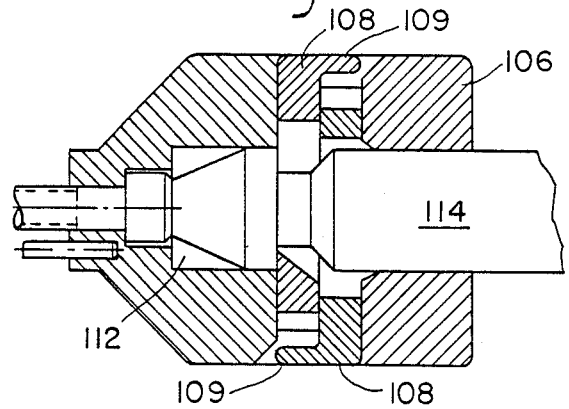
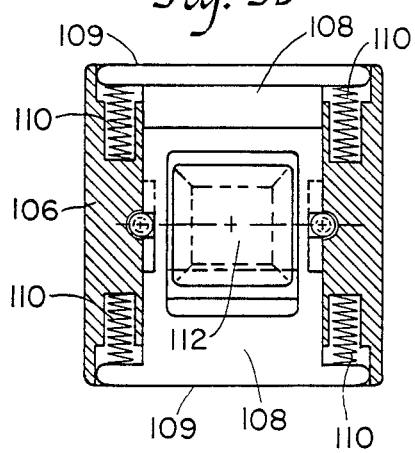
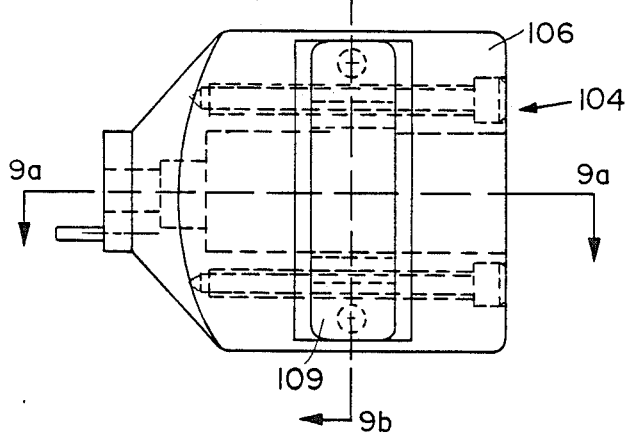
Fig. 9

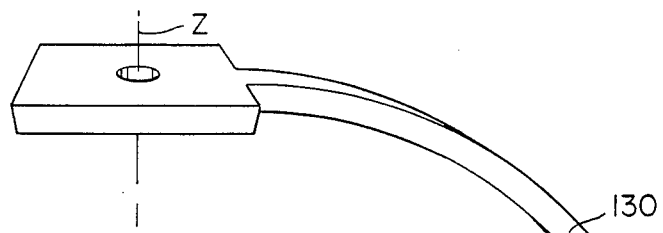
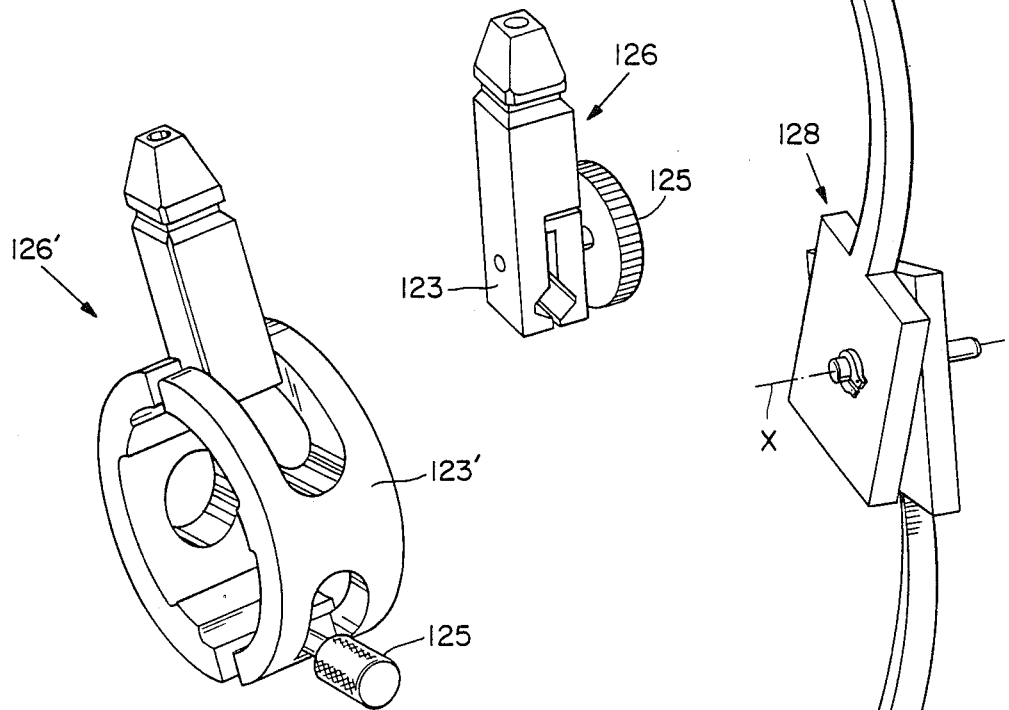
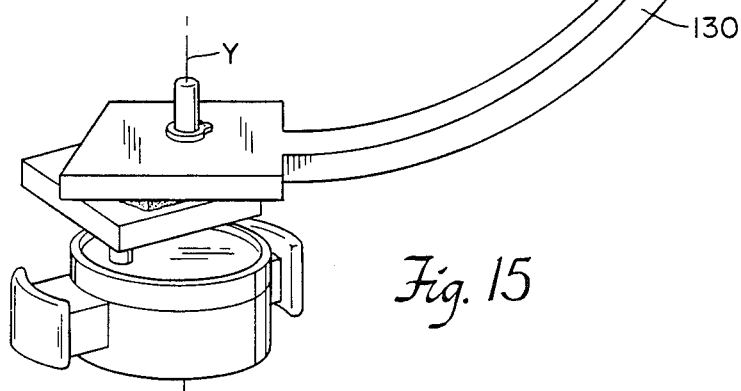

ARM DEVICE FOR ADJUSTABLE POSITIONING OF A MEDICAL INSTRUMENT OR THE LIKE

BACKGROUND OF THE INVENTION

This invention relates to devices for supporting medical instruments.

Surgical procedures, e.g., those involving arthroscopic surgery, require simultaneous use of numerous instruments by a physician. Often the procedure is complicated and one or more assistants may be required to hold one or more of the instruments in position. These assistants tend to congest the area around the operating table and restrict movement by the physician performing the surgery.

To address this problem, others have suggested arms to hold surgical equipment. For example, Milo (1975, U.S. Pat. No. 3,858,578) describes a flexible arm for holding surgical instruments, the joints of which can be simultaneously locked in place, using hydraulic pressure to tension a cable extending axially through the assembled arm elements. Poletti (1972, U.S. Pat. No. 3,638,973) and Kimoshita (1976, U.S. Pat. No. 3,986,692) describe jointed arms which can be fixed in position by hydraulic pressure.

SUMMARY OF THE INVENTION

According to the invention, in an instrument-supporting, articulated device having a distal end capable of supporting an instrument in the region of a surgical operating site, the device having at least one joint that supports a movable distal support element relative to a proximal support, the joint is associated with a mode selector, the joint having structure capable, upon selection of a first mode of operation by the selector, of enabling relatively free motion of the joint for achieving a desired position of the instrument and the joint having structure capable, upon selection of a second mode of operation by the selector, to set the position of the instrument in space with lightly loaded restraint, the lightly loaded restraint being of a value that, while the second mode continues to be selected, the user may adjust the position of the instrument by application of a light force to the instrument and upon release of such light force by the user, the instrument will remain in the newly adjusted position.

In preferred embodiments, the light force is of the order of one or a few ounces; the joint includes a vacuum-actuated restraint operable to provide the second mode of operation; the device comprises at least two joints, each having two modes of operation, the selector having at least three selectable conditions in which respectively both joints are selected to the first mode of operation both joints are selected to the second mode of operation, and a given one of the joints is selected to the first mode and other joint is selected to the second mode of operation. In one particular embodiment, the device comprises a base, a shoulder assembly having a first joint for rotation about a first axis upon the base and a second joint distal of the first joint for rotation about a second axis orthogonal to the first axis, an arm having its proximal end rotatably connected to the second joint of the shoulder assembly, and a wrist assembly connected to the distal end of the arm and having a wrist joint adapted for movement about the end of the arm, preferably the arm comprises first and second arm elements rotatably connected at an elbow joint, and, preferably, each joint has two modes of operation, more preferably, the device comprises means for delivery of vacuum into the joints, each joint comprises an instrument clamp disposed at the distal end of the device adapted to receive and fixedly hold an instrument for surgery, conduit means for delivery of vacuum through the device, and means associated with the conduit for selectively delivering vacuum into one or more of the joints to set the joints with the light restraint, preferably the means for selectively delivering vacuum comprises switch means disposed distally on the device, first conduit means for delivery vacuum into the switch means, and second conduit means for delivering vacuum from the switch means into the joints; the device further comprises counterbalance means associated with the shoulder assembly for counterbalancing the arm, preferably the counterbalancing means comprises a constant force extension spring connected at one end to the shoulder assembly, and at a second end to the arm.

In another preferred embodiment, the joint having two modes of operation comprises at least one spherical element adapted for swiveling motion and associated with a vacuum chamber in the manner that vacuum applied to the chamber draws the parts of the joint together to apply frictional restraint. Preferably, the joint comprises first and second spherical elements connected in serial sequence; the first spherical element is rigidly associated with the second spherical element; and the joint further comprises a socket for the spherical element, the wall of the socket defining a groove for receiving and supporting an o-ring in a manner to limit compression and rotation of the o-ring, the spherical element and the socket defining the vacuum chamber, establishment of vacuum in the chamber adapted to draw the spherical element into motion resisting frictional engagement with the o-ring.

According to another aspect of the invention, a surgical console comprises a multiplicity of the devices described above.

According to still another aspect of the invention, in an instrument-supporting, articulated device having a distal end capable of supporting an instrument, the device having at least one joint that supports a movable distal support element relative to a proximal support, the joint is associated with a mode selector, the joint having structure capable, upon selection of a first mode of operation by the selector, of enabling relatively free motion of the joint for achieving a desired position of the instrument and the joint having structure capable, upon selection of a second mode of operation by the selector, to set the position of the instrument in space with lightly loaded restraint, the lightly loaded restraint being of a value that, while the second mode continues to be selected, the user may adjust the position of the instrument by application of a light force to the instrument and upon release of such light force by the user, the instrument will remain in the newly adjusted position, the light force being of the order of one or a few ounces, the joint including a vacuum-actuated restraint operable to provide the second mode of operation, the device comprising: a base, a shoulder assembly having a first joint for rotation about a first axis upon the base and a second joint distal of the first joint for rotation about a second axis orthogonal to the first axis, an arm having its proximal end rotatably connected to the second joint of the shoulder assembly, counterbalance means associated with the shoulder assembly for couterbalancing the arm, and a wrist assembly connected to the distal end of the arm and having a wrist joint adapted for movement about the end of the arm, each joint having two modes of operation, the wrist joint comprising at least one spherical element adapted for swiveling motion and associated with a vacuum chamber in the manner that vacuum applied to the chamber draws the parts of the joint together to apply frictional restraint.

The invention thus provides a support for receiving an instrument, for movement of the supported instrument freely in three dimensions about the surgical site, and for holding the instrument precisely at a set position in an operating area. The joints of the device can be readily set, e.g., by application of one or more switches, but the surgeon is permitted to adjust the instrument positioning by overriding the frictional set of the joints with application of a small additional force. By using a vacuum locking mechanism, there is no risk of a component being blown off (as in hydraulic or other high pressure systems), there is no introduction of contaminated air into the operating area (as in pressurized air systems), and, if the vacuum is lost, the device does not fail immediately but rather takes at least about 30 to 60 seconds to collapse, slowly, giving the physician plenty of time to react. Other advantages of the support arm of the invention over the prior art include: the presence of a counterbalance to hold the instrument at a specific desired location within the operating area, ready to be used by a physician; the entire arm is autoclavable, so it can be touched by a physician without compromising the sterile zone; and the apparatus has a plurality of rotatable joints providing the surgeon with great flexibility to position an instrument held by the arm as he desires.

Other features and advantages of the invention will be apparent from the following description of the preferred embodiments and from the claims.

DESCRIPTION OF THE PREFERRED EMBODIMENTS

The drawings will first briefly be described.

Drawings

Figure 5:
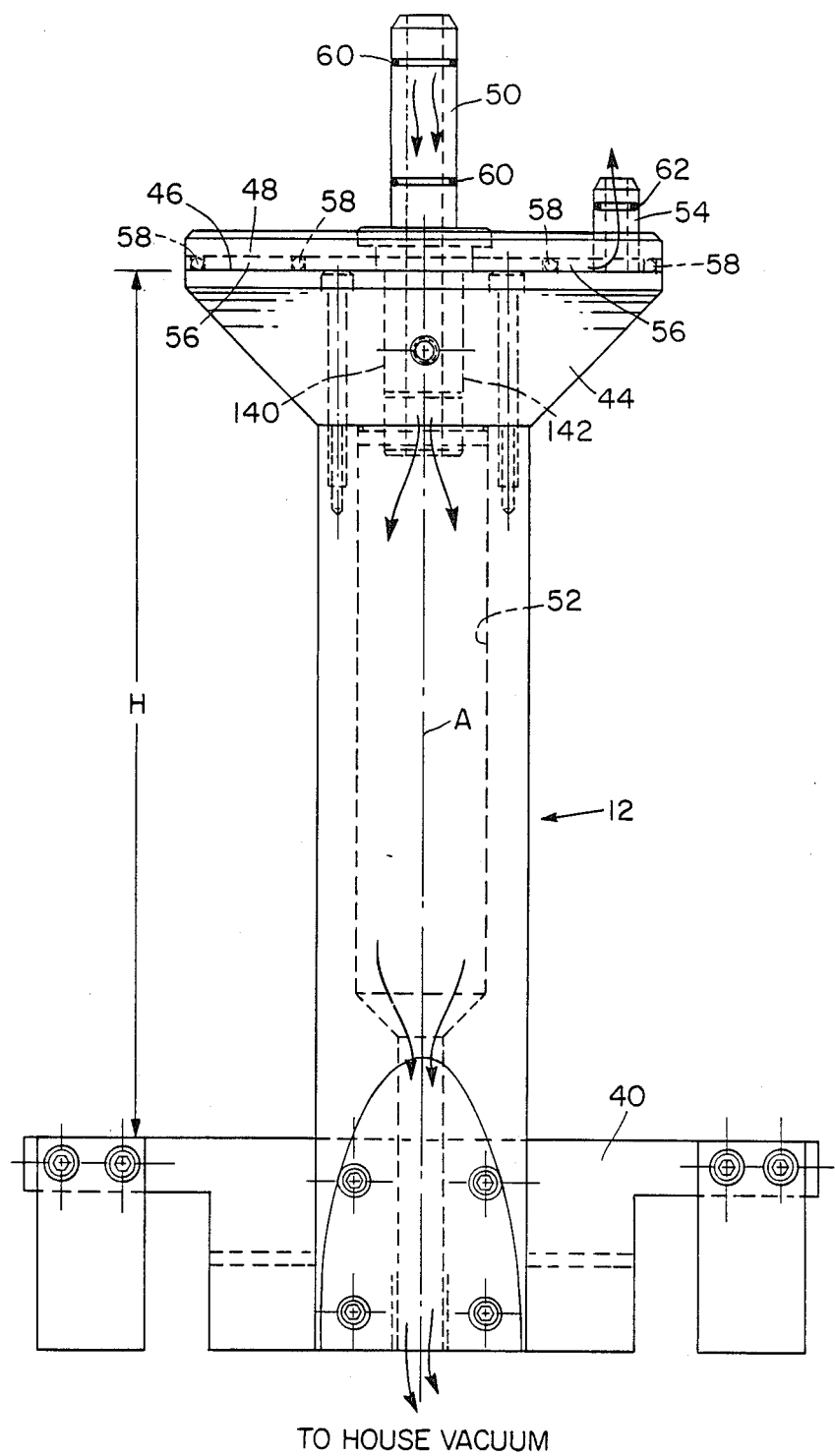
Figures 5A, 5B:
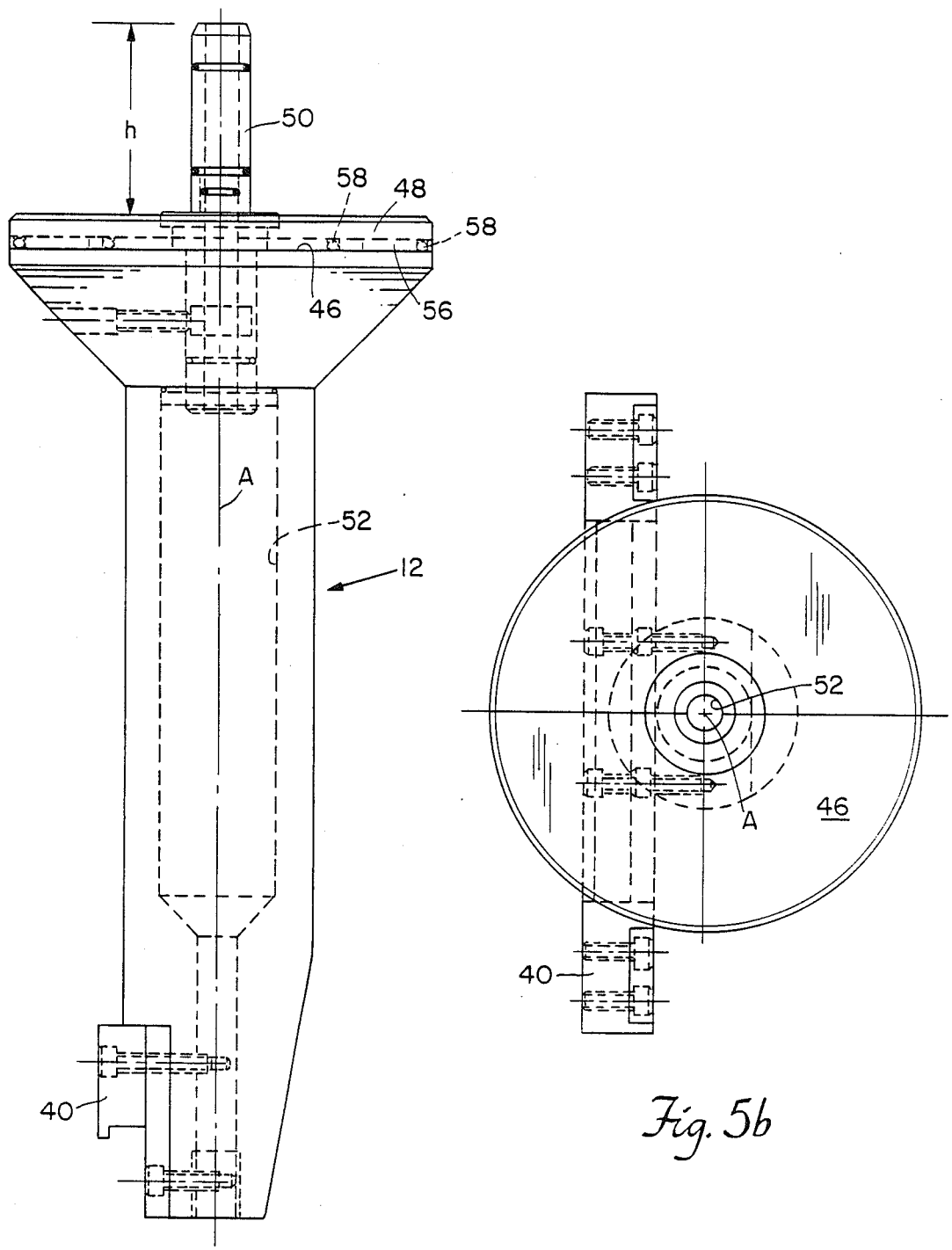
Figure 6:
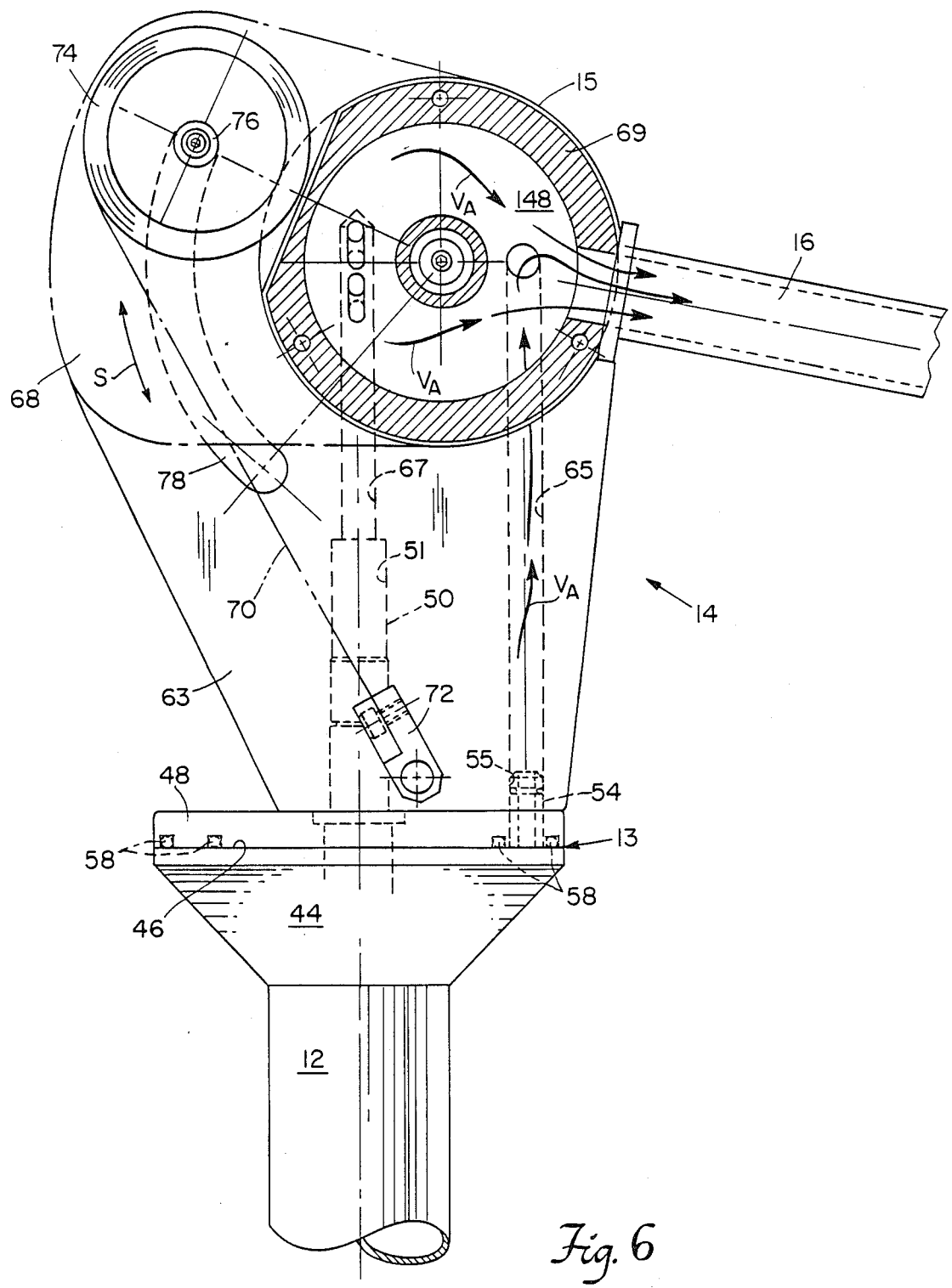
Figure 6A:
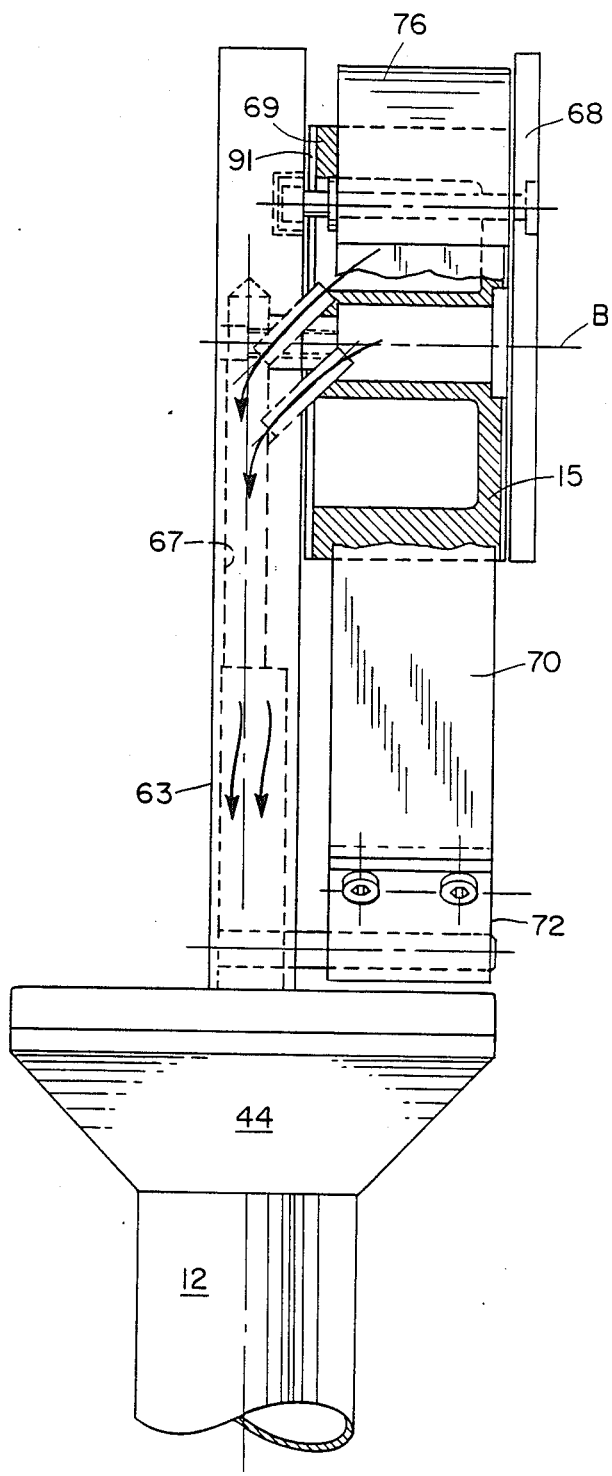
Figure 6B:
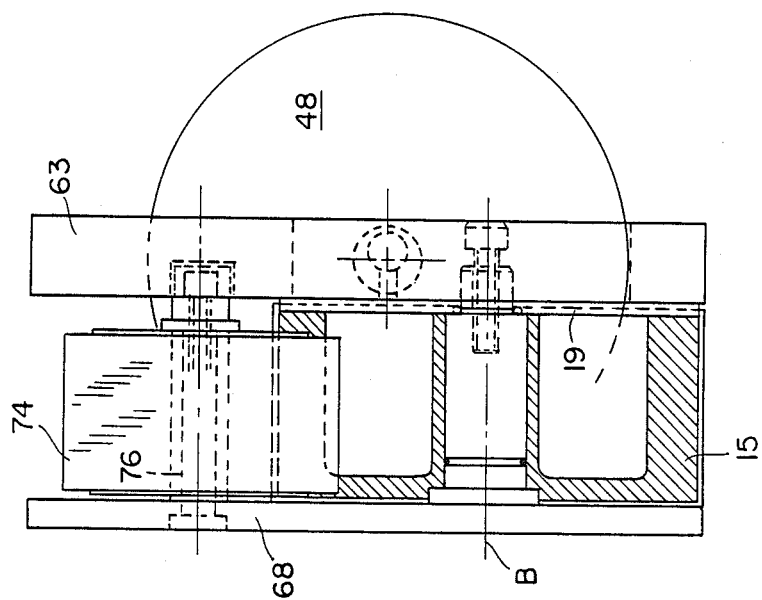
Figure 7A:
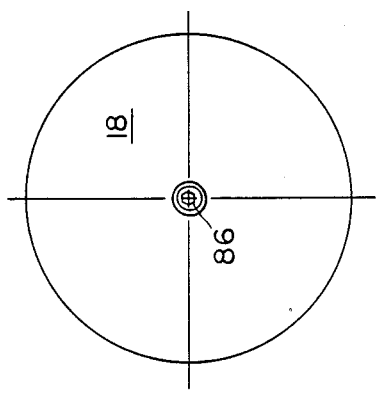
Figure 7:
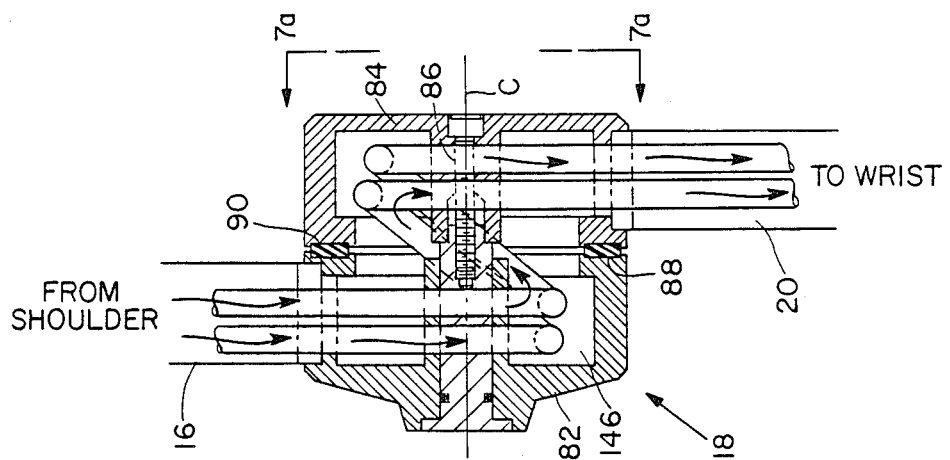
Figure 10:
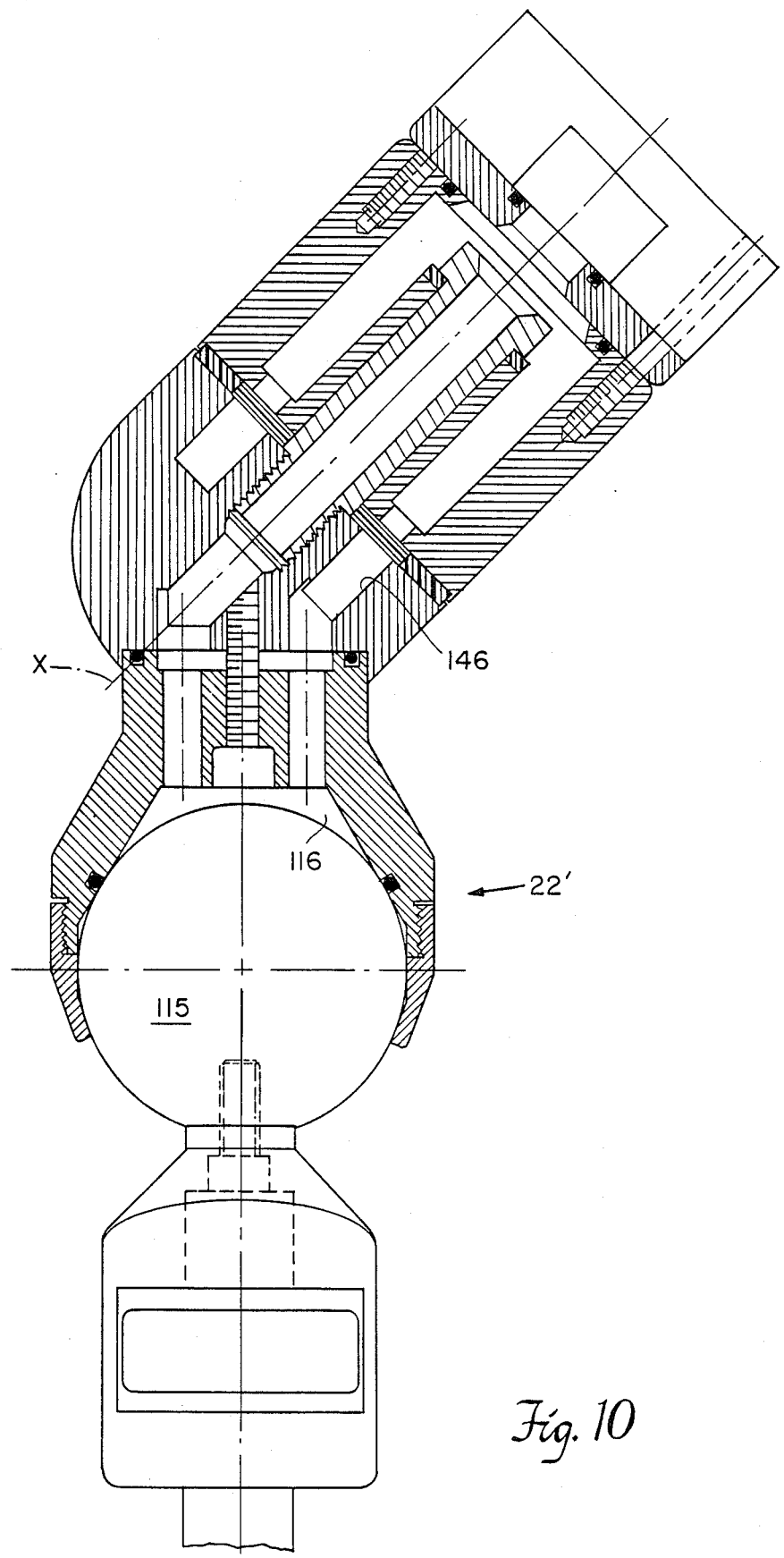
Figure 8:
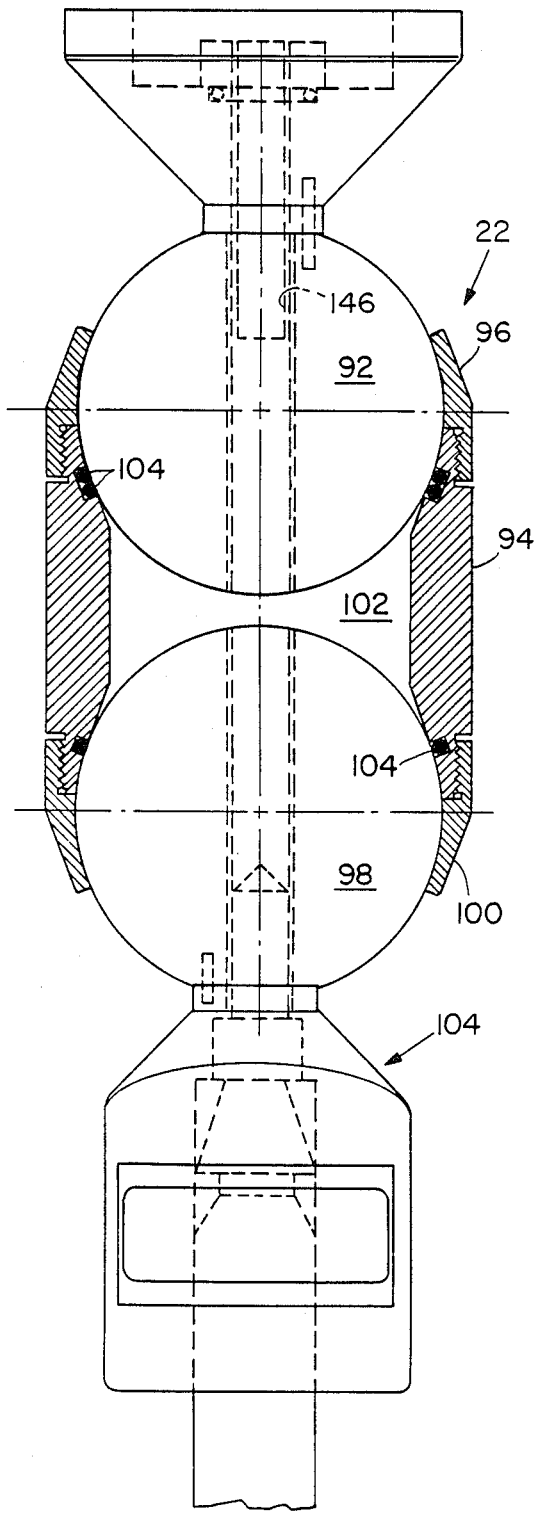
Figure 11:
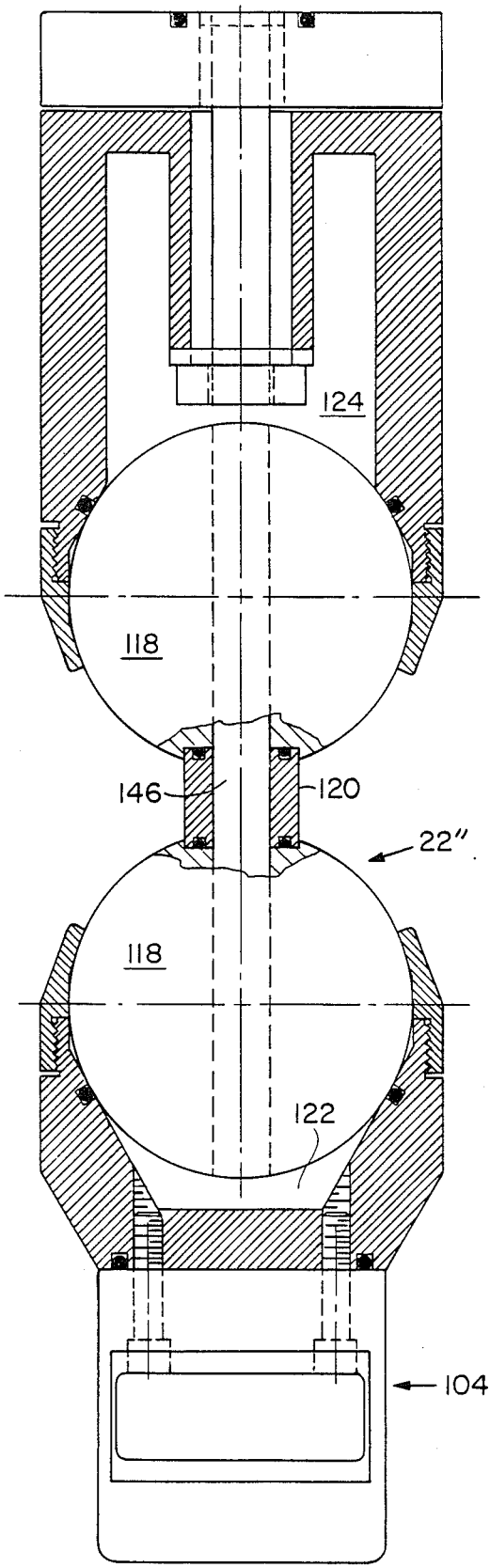
Figure 12B:
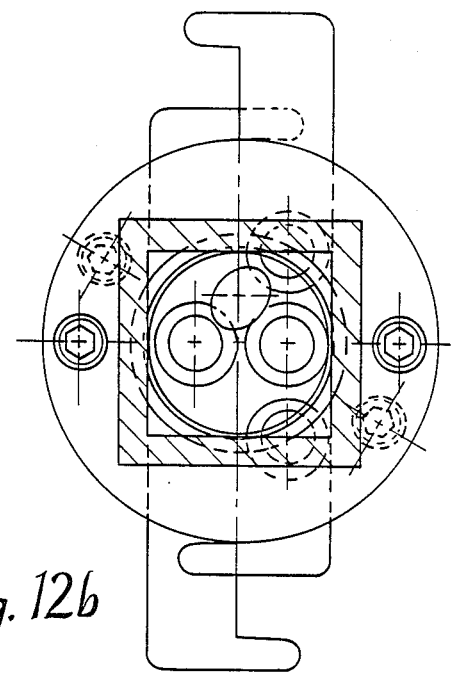
Figure 12:
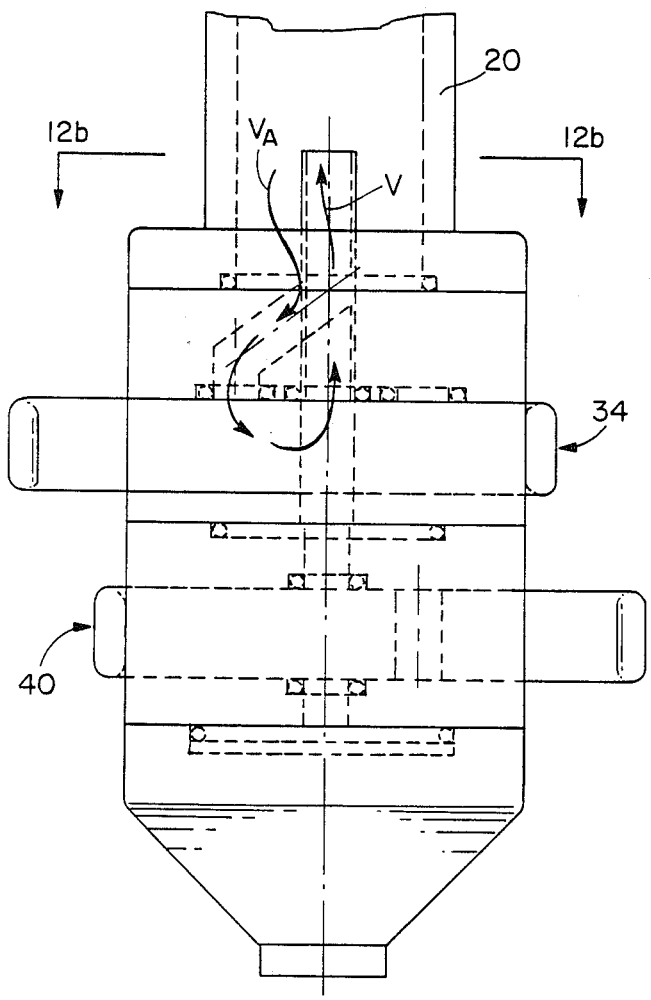
Figure 12A:
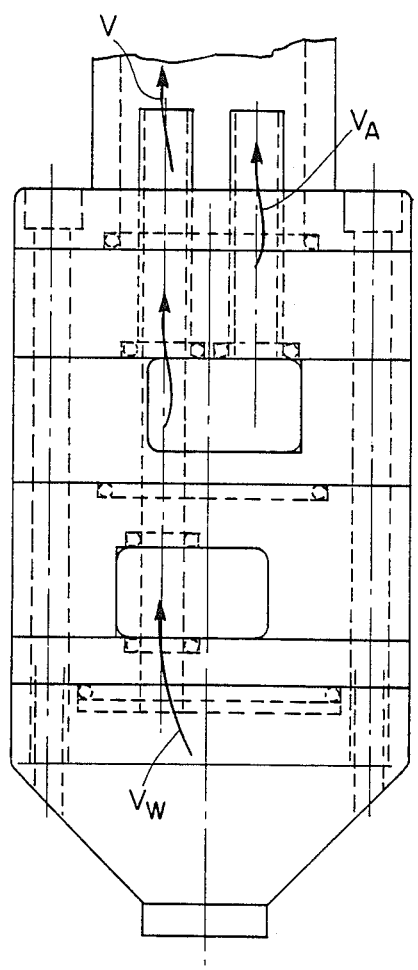
Figure 16:
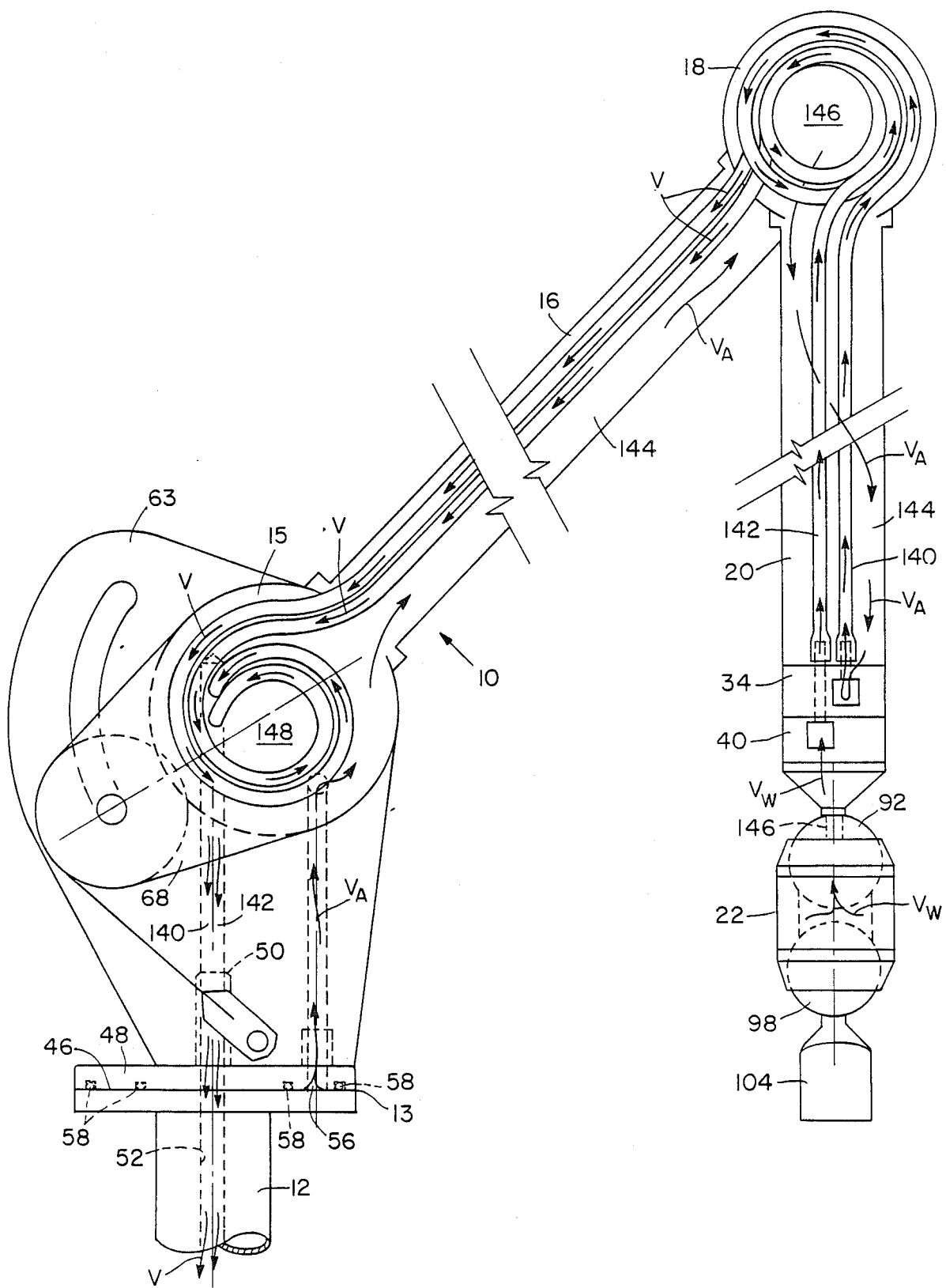
Figure 17:
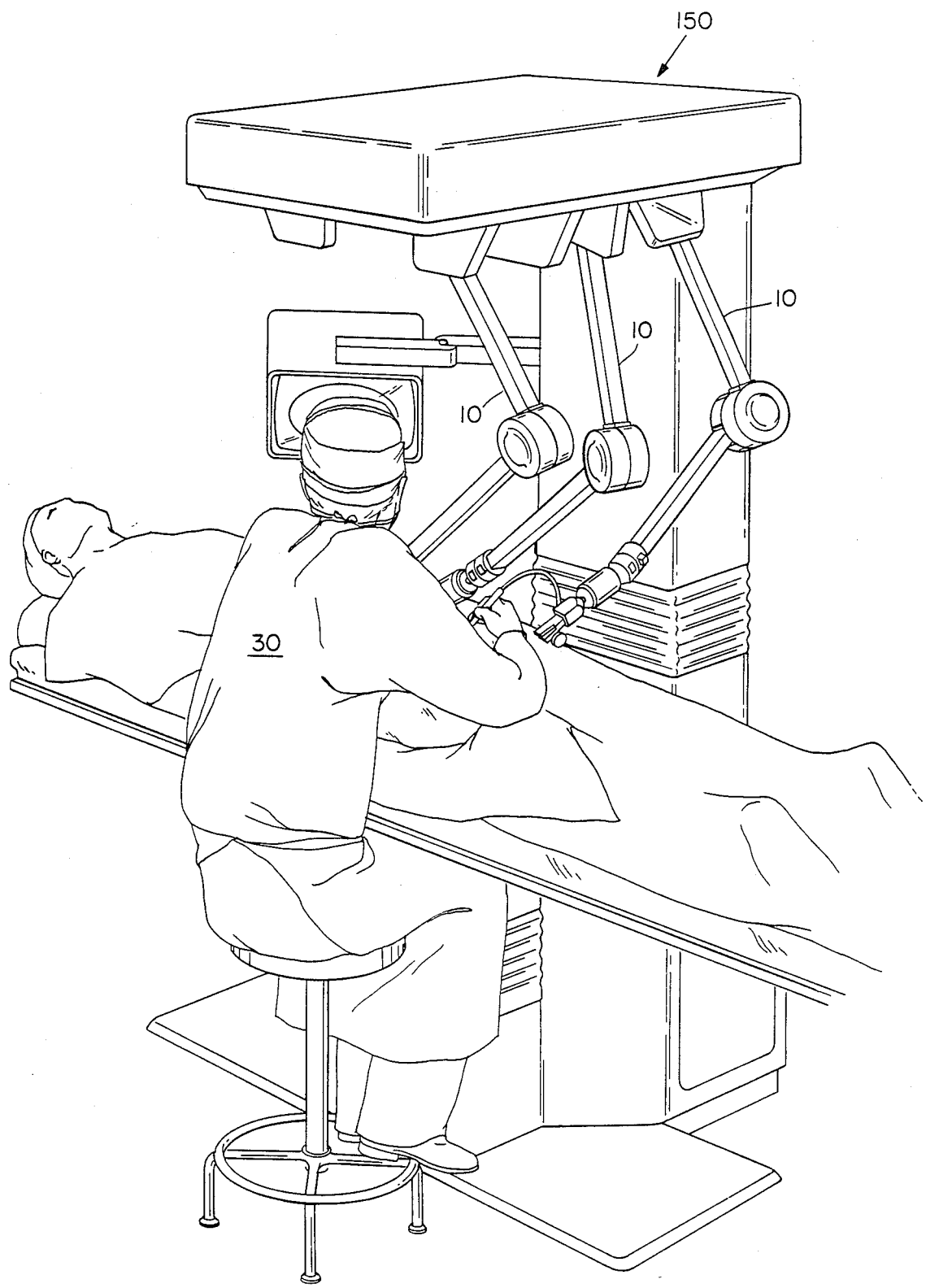

FIGS. 5, 5a, and 5b are front, side and plan views of the table mount assembly of the support arm of the invention;

FIG. 6, 6a, and 6b are front, side and plan views of the shoulder element of the device;

FIG. 7 is a side sectional view of an elbow/shoulder rotational joint of the support arm of the invention, while FIG. 7a is a plan view of the joint taken at the line 7a-7a of FIG. 7;

FIG. 8 is a side sectional view of a preferred embodiment of the wrist joint of the support arm device of the invention, with a quick disconnect assembly;

FIGS. 9, 9a and 9b are plan, and side and top sectional views of the quick disconnect assembly;

FIGS. 10 and 11 are side sectional views of alternate embodiments of the wrist joint;

FIGS. 12 and 12a are front and side views of the vacuum switch assembly, while FIG. 12b is a plan view of the switch assembly taken at the line 12b-12b of FIG. 12;

FIGS. 13, 14 are perspective views of instrument clamps for use with the device of the invention, and FIG. 15 is a perspective view of a variety a wrist joint FIG. 16 is a diagrammatic view of the support arm of the invention showing the flow of vacuum therethrough; and FIG. 17 is a somewhat diagrammatic perspective view of a surgeon employing a console having multiple support arms of the invention.

Figure 1:
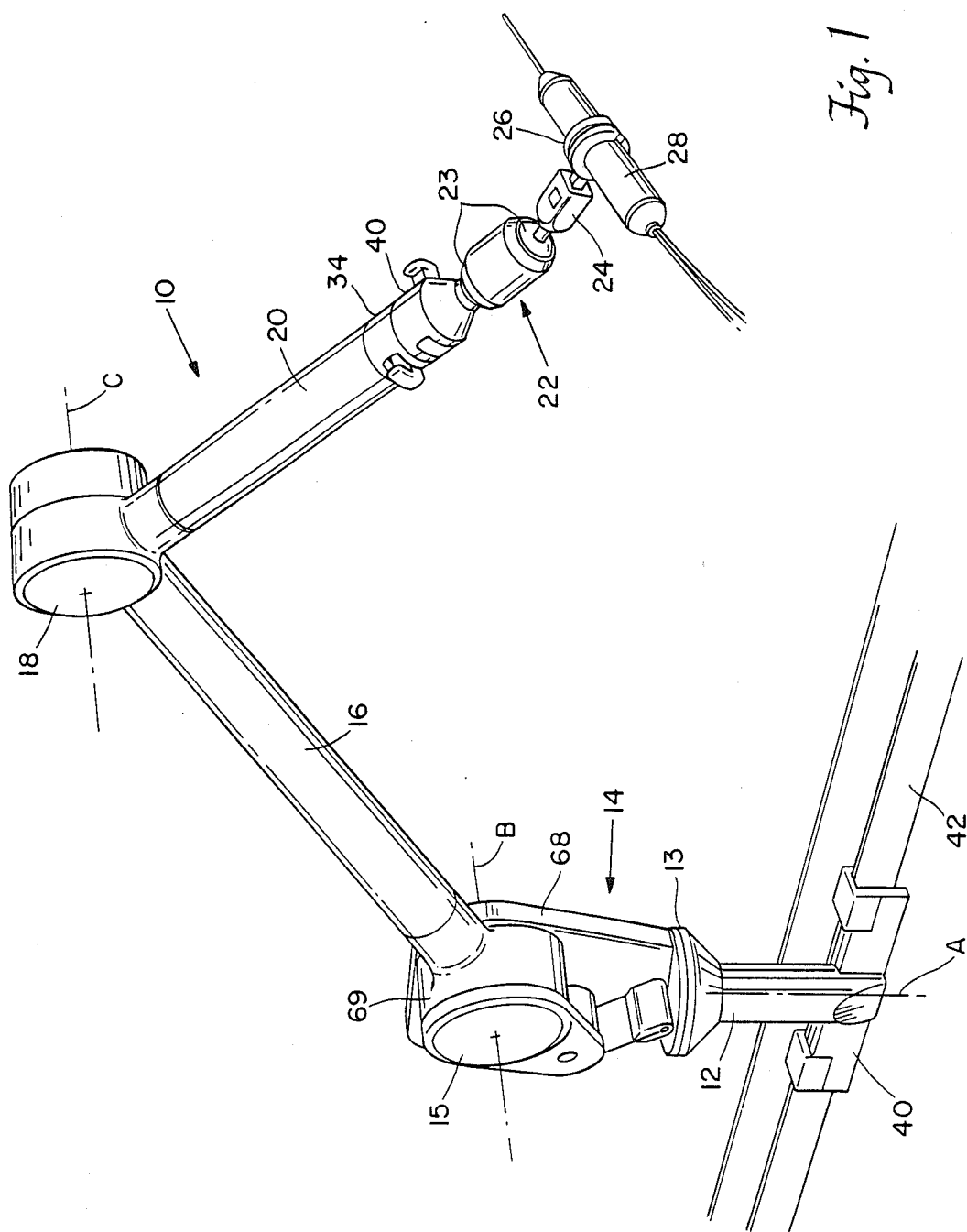
FIG. 1 is a perspective view of a support arm device of the invention.

Referring to FIG. 1, support arm 10 consists of a vertical support post 12, a shoulder assembly 14 constructed for rotation at 13 about axis A, and including a shoulder joint 15 constructed for rotation about axis B; upper arm 16; elbow joint 18 constructed for rotation about axis C; forearm 20; and wrist assembly 22, including a wrist joint 23, e.g., a pair of spherical joints adapt to swivel independently of each other. At the end of the wrist assembly there is provided a quick disconnect assembly 24 for receiving an instrument clamp 26 holding instrument 28, e.g., a powered surgical instrument. The entire arm is steam autoclavable for use in the surgical area without draping.

The structure of the support arm device will be described in more detail below, but first we describe the use of the invention for better understanding of its important features.

The invention better permits the surgeon to act as an orchestra leader, directing his surgical team through a procedure, by providing a surgeon with the ability to precisely position an instrument, e.g., a powered surgical instrument or an endoscopic camera, for a surgical procedure and allowing him to leave the instrument supported exactly at that position, thus freeing a hand that would otherwise be required to hold the instrument during the procedure, typically the surgeon's own, or in some instances that of an assistant, in which case the assistant would likely impede access to the surgical site. The surgeon, free of having to hold the instrument in position, can use the hand for other purposes, e.g., to better employ tactile control or monitoring of the patient, e.g., in positioning or manipulating the limbs. The support arm allows the surgeon to leave the surgical area, e.g., to consult x-rays or patient records, and return to the procedure with his instruments positioned exactly as he left them. The procedure is thus enhanced and is also shortened.

Figure 2:
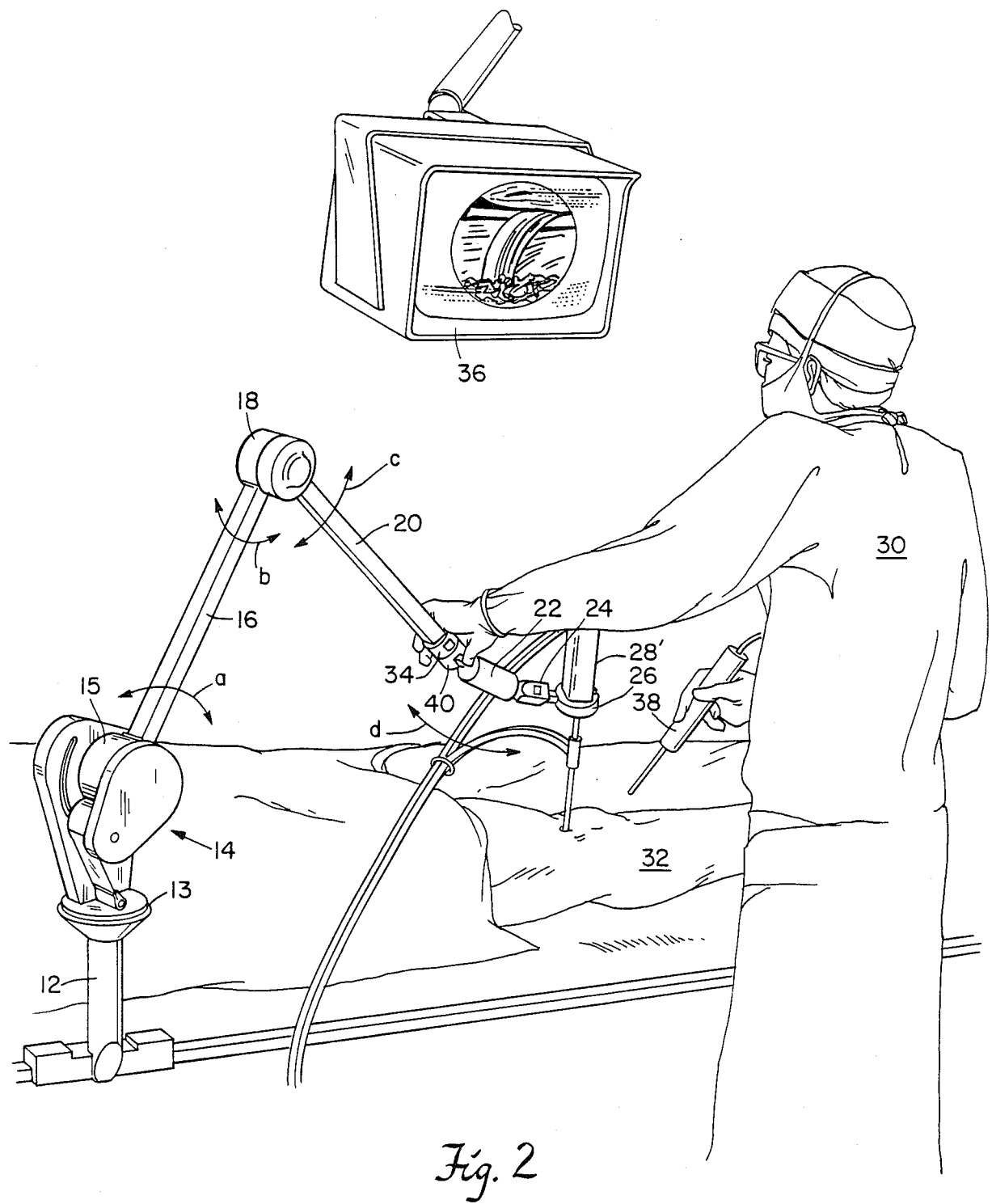
FIGS. 2, 3 and 4 are somewhat diagrammatic perspective views of a surgeon employing the support arm device of the invention for positioning an instrument during surgery.

Referring to FIG. 2, the support arm 10 of the invention, in a first mode of operation, allows the surgeon 30 to move the arm freely to position the surgical instrument, in this case an endoscopic camera 28', at a desired location about the surgical site, e.g., as shown in the figure, a patient's knee 32, with the shoulder 13 and shoulder joint 15, elbow joint 18 and wrist joint 23 all free to move, as indicated by arrows a, b, c and d. Once the instrument is grossly positioned, the surgeon sets the shoulder 13, elbow joint 18 and shoulder joint 15 by activating a first switch 34 adjacent the wrist assembly.

Figure 3:
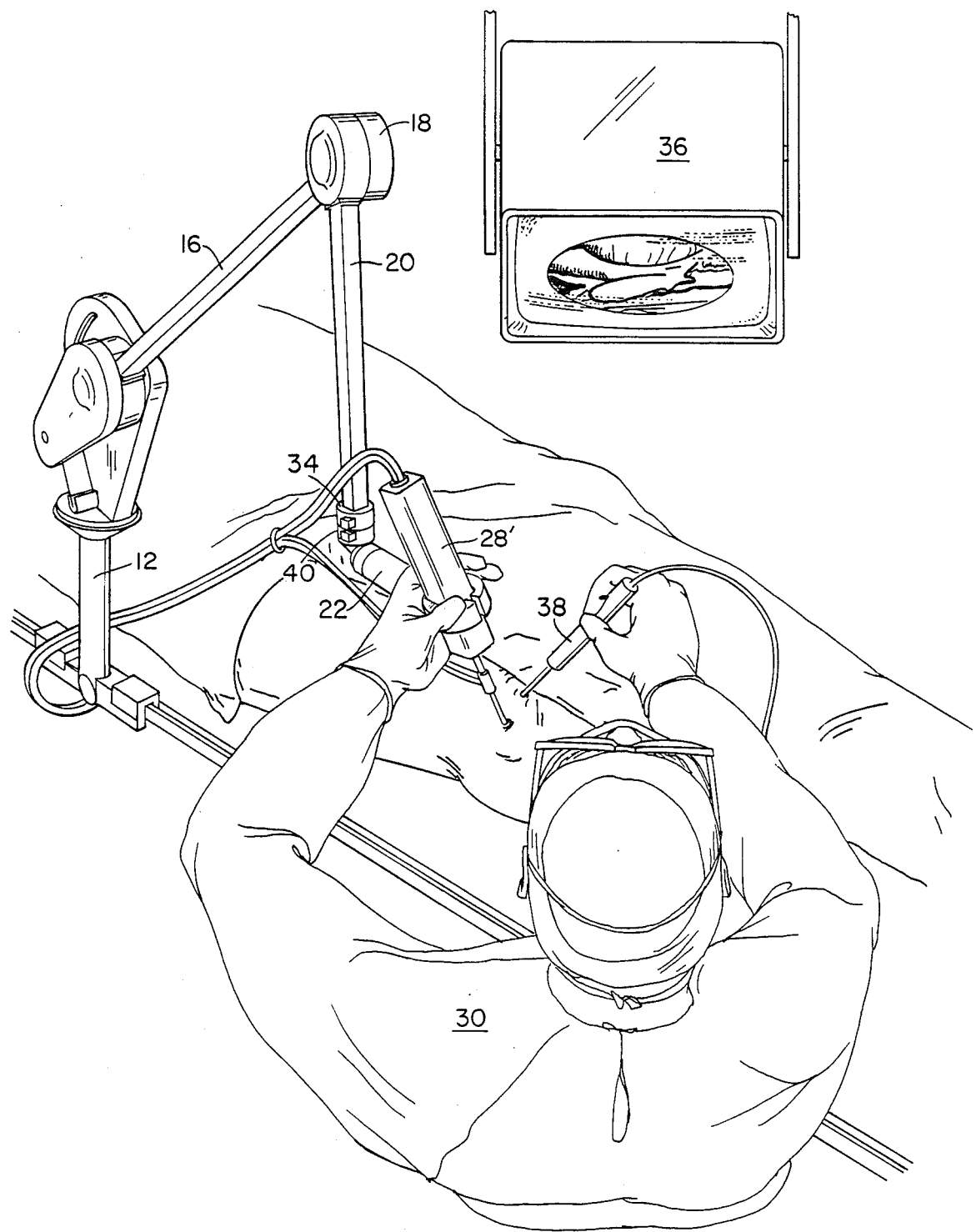

Referring now to FIG. 3, the surgeon 30 fine tunes the position of the instrument 28', while observing the video monitor 36 and manipulating another instrument, e.g., a powered surgical tool 38, with his other hand. The ability to fine tune the position of the instrument is provided by the free operation of the wrist joint 23, and also by the ability of the surgeon, as desired, to override the vacuum frictional set of the elbow and shoulder joints 15, 18 and the shoulder 13 by application of slight additional force. (Of course if more adjustment of the shoulder and elbow and shoulder joints is required, the surgeon may quickly free these joints by activating switch 34, adjusting the position and resetting these joints.) Once the desired fine tune position of the instrument is achieved, the surgeon sets the wrist joint by activation of second switch 40 (FIG. 3), also adjacent the wrist assembly.

Figure 4:
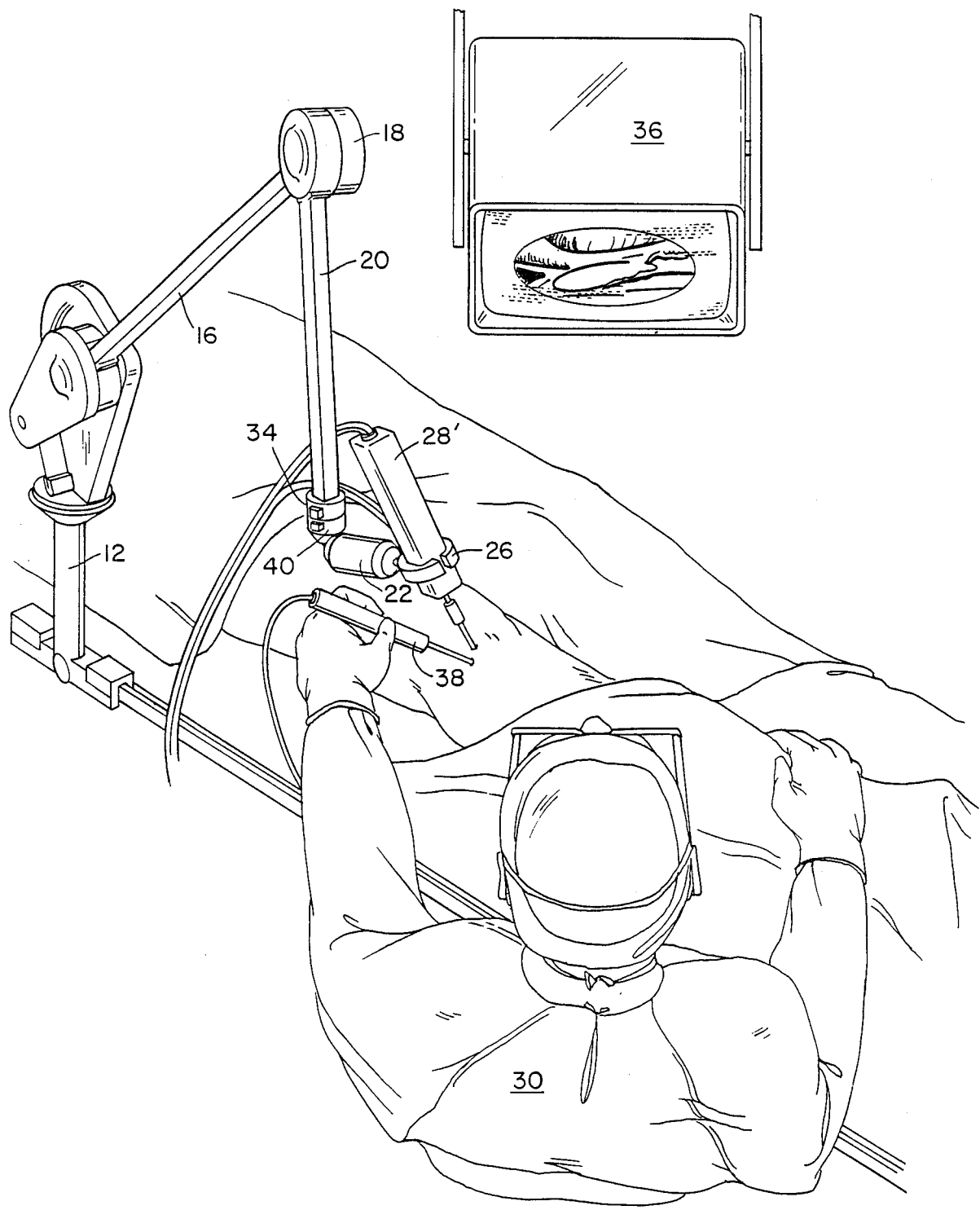

Once the instrument is set in position, the surgeon has his hand free for other activity in the surgical site. For example, in FIG. 4, the support arm device of the invention supports endoscopic camera 28' at a position to provide the surgeon with the desired view on the monitor 36. The surgeon with his left hand manipulates a surgical tool, e.g., a powered shaving or cutting instrument 38, and with his right hand grasping the patient's ankle manipulates the limb to establish varus or valgus stress in the knee joint for improved accessibility.

During the surgical procedure, the surgeon may quickly adjust the position of the instrument, either by deactivating the vacuum through one or the other of switches 34, 40, or by applying a small additional amount of force, e.g., of the order of one or a few ounces to override the vacuum set of one or more of the joints, to move the instrument as desired. This feature results from the use of vacuum to set the joints frictionally, opposed to mechanical-type locking joints that freeze position. As will be described, the instrument is always supported by the arm to some extent, even when the joints are not set by vacuum, thus reducing physician fatigue as well.

Although the drawings so far described illustrate an arthroscopic procedure of the knee, it will be recognized that the support arm has wide application for surgery and other areas of medicine, e.g., in arthroscopic surgery of all surgical joints, e.g., oral, arthropaedic and podiatric, and also in the fields of ophthalmology and neuro surgery, and generally in any procedure in which the physician will be aided by a readily adjustable means for fixedly positioning an instrument of any type in the surgical field; for example, in procedures requiring the physician to position a treatment instrument and withdraw during treatment application, e.g., treatment by proton rays.

Referring now to FIG. 1, and also to FIGS. 5, 5a and 5b, post 12 extends upwardly a distance, H, e.g., about 12 inches, from clamp 40 constructed for secure attachment along a surgical bed rail 42 (FIG. 1). The post 12 has a conical upper segment 44 terminating in a flat horizontal surface 46. Disposed upon surface 46 is a plate element 48 constructed for rotation about vertical stud 50 extending upwardly along axis A from post 12. The post and stud 50 define a conduit 52 for vacuum from an external source, through the base of the post, as will be described more fully below. A second vertical stud 54, disposed through plate 48 at a position readily outward of axis A, defines a conduit for vacuum into chamber 56 defined between opposed surfaces of plate 48 and post 12, and sealed by o-rings 58.

As best seen in FIGS. 6, 6a and 6b, shoulder assembly 14 consists of a vertical plate 63 having apertures 51, 55 to receive studs 50, 54 in vacuum tight relationship (provided by o-rings 60, 62 about the studs), and defining vacuum conduits 65, 67 therethrough, as described below. Stud 50 is of sufficient height, h, e.g., about two inches, to support the shoulder and extended portions of the arm against bending or tipping under load. The second stud 54 causes the shoulder and plate to rotate together, at 13. The shoulder further consists of shoulder joint 15 having a shoulder joint element 69 mounted for rotation relative to shoulder plate 63 on axis 13, the joint element being connected to the inner end of upper arm 16. Affixed for rotation with the joint element 69 is a counter-balance plate 68. Movement of arm 16 is resisted by a constant force extension spring 70 attached at one end 72 to the shoulder plate 63 and having a coiled end 74 attached to a shaft 76 extending between plate 68 and an arcuate groove 78 defined in the plate 63. The shaft thereby is caused to move with upper arm 16, movement of arm 16 (indicated by arrow S) causing the spring to uncoil and exert force to resist further movement of the arm. The shaft 76 to which spring coil 74 is attached is restricted to movement in the groove, thereby limiting the range of motion of the upper arm, e.g., to about 10° below horizontal to 100°, or over other ranges as desired.

Referring now to FIG. 7, the elbow joint 18, between upper arm 16 and forearm 20, consists of first and second rotating joint elements 82, 84, each connected to one arm, and adapted to pivot about axis C, on pin 86. Disposed in an annular groove 88 defined between the rotating joint elements is a washer, e.g., rubber or silicone, 90, which in the presence of a vacuum condition within the joint restricts relative movement of the joint elements, as described more fully below. The rotary joint at the shoulder is similarly constructed.

Referring to FIG. 8, at the outer end of the forearm 20 there is disposed wrist assembly 22, in the preferred embodiment shown consisting of a first spherical element 92 attached to the end of forearm 20 and held within a cylindrical sleeve 94 by threaded ring 96. A second spherical element 98 is held in the opposite end of the cylindrical sleeve by ring 100, the spherical elements defining a vacuum chamber 102 therebetween, sealed by o-rings 104 held in grooves sized to restrict compression and resist rotation of the o-ring.

Referring to FIGS. 9, 9a and 9b, at the outer end of spherical element 98 there is provided a quick disconnect assembly 104 having a body 106 and a pair of push bars 108 held in position by compression springs 110. For receiving the shaft 114 of an instrument clamp, e.g., as shown in FIGS. 13 and 14, the body and bars define a cavity 112. As the male shaft is inserted, the bars are urged radially outwardly to allow passage; the springs then return the bars to the position of FIG. 9a to secure the clamp. To change instruments as desired, the surgeon merely presses the exposed surfaces 109 of bars 108 to release the clamp.

Other embodiments of the wrist joint are shown in FIGS. 10 and 11. In FIG. 10, a wrist element 22' has a single spherical element 115 defining vacuum chamber 116 at the outer end of the forearm, and is attached to the forearm at an angle to the axis X of the arm. In the wrist joint 22" of FIG. 11, a pair of spherical elements 118 are provided, connected by a rigid hollow shaft 120. Each spherical element defines, with structure respectively adjacent the arm 20 and the quick disconnect assembly 104, separate vacuum chambers 122, 124 connected through the shaft. In another embodiment, the wrist joint may comprise a series of four vacuum lockable rotary joints sequentially arranged at right angles and rotatable about respective axes.

Referring to FIGS. 12, 12a and 12b, vacuum actuator switches 34, 40 consist of slide switches positioned at the outer end of forearm 20, adjacent wrist assembly 22. Switch 34 in a first position allows vacuum drawn through conduit 140 to be diffused through the body of the switch element. In a second position of the slide switch (shown in FIG. 12), vacuum $V_A$ is directed into conduit 144 to draw vacuum in the elbow and shoulder of the arm. Switch 40 in a first position (shown in FIG. 12) prevents vacuum from being drawn through conduit 146, instead diffusing vacuum in the body of the switch element. In a second position of switch 40, vacuum $V_W$ is drawn in conduit 146 to set the joints of the wrist.

Referring briefly to FIGS. 13 and 14, typical instrument clamps 126, 126' are shown. The clamps consist of a shaft 114 sized and constructed to be received by quick disconnect assembly 104, and a clamp, e.g., a tong clamp 123 (FIG. 13) or a ring clamp 123' (FIG. 14). The clamps, constructed for the particular instrument with which they are to be employed, are tightened about the instrument by means of threaded knobs 125. In FIG. 15 there is shown a wrist joint variant 128 for use in particular surgical procedures requiring multiple instruments to be disposed on axes X, Y and Z of the device directed at the center of a sphere defined by arms 130, e.g., for drilling into a joint from outside the body along axis Z, to intercept a probe on axis X.

Referring now to FIGS. 16, the operation of the support arm 10 of the invention in the several modes of operation will be described. Vacuum (indicated by arrows, V) is provided from an external source, e.g., wall vacuum in an operating room (not shown) typically about 18 to 22 mm Hg, into the base of post 12. The post defines a conduit 52 for flow of vacuum to stud 50. A pair of separate conduits, e.g., plastic tubes 140, 142, extend through stud 50 into shoulder plate 63 and from there through shoulder joint 15, upper arm 16, elbow joint 18, and forearm 20 to switches 34, 40 adjacent wrist assembly 22. When switches 34, 40 are open, air is drawn out of the operating room into the support arm, and all the joints are free to move allowing the surgeon to move the instrument freely for gross adjustment. (By use of vacuum, there is no danger of fluid, either liquid or gas, being expelled into the surgical environment, as with pneumatic or hydraulic pressure devices.) When switch 34 is closed, vacuum $V_A$ is drawn in closed return conduit 144 creating a vacuum condition in chambers defined by the elbow joint (146), the shoulder joint (148) and at the shoulder (56). Those chambers are sealed, the shoulder by o-rings 58, the elbow and shoulder joints by washers 90, 91 and the plate 48 is drawn toward the surface 46 against the o-rings to resist rotation at 13, and the joint elements 82, 84 of the elbow and the joint elements of the shoulder are drawn together against the washers to similarly resist rotation of the elbow and shoulder joints. (The resistance force is frictional, and can be overcome by application of a slightly greater force, e.g., by the surgeon, for minor adjustments of instrument position.)

Actuation of slide switch 40 draws a vacuum $V_W$ via conduit 146 into the chamber (or chambers) of the wrist joint to draw the spherical elements 92, 98 into frictional engagement with the o-rings 104, thereby setting the wrist joint, but in a manner that may be overcome by application of a relatively small force, e.g., one or just a few ounces, for adjustment of the instrument.

Other embodiments are within the following claims, for example, in FIG. 17 there is shown a console 150 provided with several arms 10 of the invention for supporting multiple means for assisting the surgeon during the procedure to be performed. The device of the invention may employ vacuum, e.g., down to about 16 mm Hg, or the joints may operate electronically or by mechanical means. Vacuum may be provided by a stand-alone pump, or by a venturi-arrangement operating from a pressure source.

What is claimed is:

1. An articulated instrument-supporting device for placement and manipulation of an instrument within a predetermined region of space, comprising
    a set of device arm components, arranged in series and extending from a proximal support base, at least a pair of adjacent said arm components joined at an articulating joint,
    said articulating joint comprising a first rigid joint element joined to a first arm component and a second rigid joint element joined to a second arm component adjacent to said first arm component, said first and second rigid joint elements defining opposed joint surfaces which define, with a surrounding housing, a joint capsule, and seal means disposed between said joint surfaces and said housing, said first and second joint elements adapted for axial movement within said housing, between a first mode position and a second mode position,
    means at a distal end of said device for receiving and gripping an instrument,
    a source of fluid pressure,
    conduit means for connecting said joint capsule to said source of fluid pressure,
    means for selective actuation of the connection between said joint capsule to said source of fluid pressure,
    in a first mode, said means for selective actuation obstructing the connection of said joint capsule to said source of fluid pressure, thereby to permit relatively free motion of said first and second arm components about said joint for macro-adjustment of an instrument supported by said device, and,
    in a second mode, said means for selective actuation freeing the connection of the source of fluid pressure to said joint capsule, thereby to continuously connect said source of fluid pressure to said joint capsule to cause said first and second rigid joint elements to move axially for frictional engagement of surfaces of said joint elements upon said seal means in a manner to frictionally set the relative positions of said first and second arm components with a lightly loaded restraint of value selected to support an instrument within a predetermined region of space, the value of restraint by frictional engagement of said surface upon said seal members being further selected to allow a user to micro-adjust instrument position by application of light adjusting force to the instrument with said source of fluid pressure continuously applied to said joint capsule, the device supporting the instrument in the new position upon release of the light adjusting force.

2. The articulated instrument-supporting device of claim 1 wherein said source of fluid pressure comprises a vacuum.

3. An articulated instrument-supporting device for placement and manipulation of an instrument within a predetermined region of space, comprising
    a set of device arm components, arranged in series and extending from a proximal support base, at least a pair of adjacent said arm components joined at an articulating joint, said articulating joint comprising a first rigid joint element joined to a first arm component and a second rigid joint element joined to a second arm component adjacent to said first arm component, said first and second rigid joint elements defining opposed joint surfaces which define, with a surrounding housing, a joint capsule, and seal means disposed between said joint surfaces and said housing, said first and second joint elements adapted for axial movement within said housing, between a first mode position and a second mode position, means at a distal end of said device for receiving and gripping an instrument, a source of fluid pressure comprising a vacuum, conduit means for connecting said joint capsule to said source of fluid pressure, means for selective actuation of the connection between said joint capsule to said source of fluid pressure, in a first mode, said means for selective actuation obstructing the connection of said joint capsule to said source of fluid pressure, thereby to permit relatively free motion of said first and second arm components about said joint for macro-adjustment of an instrument supported by said device, and, in a second mode, said means for selective actuation freeing the connection of the source of fluid pressure and said joint capsule in a manner to cause said first and second rigid joint elements to move axially for frictional engagement of surfaces of said joint elements upon said seal means in a manner to frictionally set the relative positions of said first and second arm components with a lightly loaded restraint of value selected to support an instrument within a predetermined region of space, the value of restraint by frictional engagement of said surface upon said seal members being further selected to allow a user to micro-adjust instrument position by application of light adjusting force to the instrument, the device supporting the instrument in the new position upon release of the light adjusting force.

4. The articulated instrument supporting device of claim 1 or 3 wherein said articulating joint is disposed closely adjacent to said means for receiving and gripping an instrument at the distal end of said device.

5. The device of claim 1 or 3 wherein said light adjusting force is of the order of one or a few ounces.

6. The device of claim 1 or 3 comprising at least two said joints, each having said two modes of operation, the means for selective actuation having at least three selectable conditions in which, respectively, both joints are selected to the first mode of operation, both joints are selected to the second mode of operation, and a given one of said joints is selected to the first mode and the other joint is selected to the second mode of operation.

7. An articulated instrument-supporting device for placement and manipulation of an instrument within a predetermined region of space, comprising a set of device arm components, arranged in series and extending from a proximal support base, adjacent arm components of said set joined at at least two articulating joints, each said articulating joint comprising a first rigid joint element joined to a first arm component and a second rigid joint element joined to a second arm component adjacent to said first arm component, said first and second rigid joint elements defining opposed joint surfaces which define, with a surrounding housing, a joint capsule, and seal means disposed between said joint surfaces and said housing, said first and second joint elements adapted for axial movement within said housing, between a first mode position and a second mode position, means at a distal end of said device for receiving and gripping an instrument, conduit means for connecting each said joint capsule to a source of fluid pressure, means for selective actuation of the connection between each said joint capsule to said source of fluid pressure, said means for selective actuation, in a first mode of each said joint capsule, obstructing the connection of said joint capsule to said source of fluid pressure, thereby to permit relatively free motion of said first and second arm components about said joint for macro-adjustment of an instrument supported by said device, and said means for selective actuation, in a second mode of each said joint capsule, freeing the connection of the source of fluid pressure and said joint capsule in a manner to cause said first and second rigid joint elements to move axially to engage upon said seal means thereby to set the relative positions of said first and second arm components with a lightly loaded restraint of value selected to support an instrument within a predetermined region of space and to allow a user to micro-adjust instrument position by application of light adjusting force to the instrument, the device supporting the instrument in the new position upon release of the light adjusting force, said means for selective actuation having at least three selectable conditions in which, respectively, two joints are selected to the first mode of operation, both joints are selected to the second mode of operation, and a given one of said joints is selected to the first mode and the other joint is selected to the second mode of operation.

8. The device of claim 1, 3 or 7 comprising:

a shoulder assembly having a first joint for rotation about a first axis upon said support base and a second joint distal of the first joint for rotation about a second axis orthogonal to said first axis, an arm having its proximal end rotatably connected to said second joint of said shoulder assembly, and a wrist assembly connected to the distal end of said arm and having a wrist joint adapted for movement about the end of said arm.

9. The device of claim 8 wherein said arm comprises first and second arm elements rotatably connected at an elbow joint.

10. The device of claim 8 wherein each of said joints has said two modes of operation.

11. The device of claim 8 further comprising counterbalance means associated with said shoulder assembly for counterbalancing said arm.

12. The devices of claim 11 wherein said counterbalancing means comprises a constant force extension spring connected at one end to said shoulder assembly, and at a second end to said arm.

13. The device of claim 1, 3 or 7 wherein said joint having two modes of operation comprises at least one spherical element adapted for swiveling motion, an associated vacuum chamber, and means for applying vacuum to said chamber to draw parts of the joint together to apply frictional restraint.

14. The device of claim 13 wherein said joint comprises first and second spherical elements connected in serial sequence.

15. The device of claim 13 wherein said joint further comprises a socket for said spherical element, said socket having a wall defining a groove for receiving and supporting an o-ring in a manner to limit compression and rotation of said o-ring, said spherical element and said socket defining said vacuum chamber, establishment of vacuum in said chamber adapted to draw said spherical element into motion resisting frictional engagement with said o-ring.

16. A surgical console comprising a multiplicity of the devices of claim 1 or 7.

* * * * *

UNITED STATES PATENT AND TRADEMARK OFFICE
CERTIFICATE OF CORRECTION

PATENT NO. : 4,863,133
DATED : September 5, 1989
INVENTOR(S) : Leonard Bonnell

It is certified that error appears in the above-identified patent and that said Letters Patent are hereby corrected as shown below:

Col. 4, line 3, "FIGS. 13,14" should be --FIGS. 13 and 14--.

Col. 4, line 5, "variety a" should be --variant of a--.

Col. 5, line 56, "readily" should be --radially--.

Col. 10, line 59, "devices" should be --device--.

Signed and Sealed this

Thirteenth Day of November, 1990

Attest:

HARRY F. MANBECK, JR.

Attesting Officer

Commissioner of Patents and Trademarks